United States Patent [19]
Wong et al.

[11] Patent Number: 6,143,714
[45] Date of Patent: *Nov. 7, 2000

[54] METHODS OF USING HEPATOCYTE GROWTH FACTOR TO PROMOTE SURVIVAL, GROWTH AND DIFFERENTIATION OF MOTOR NEURONS

[75] Inventors: Vivien Wong, Scarsdale; Gregory Conn, Bedford Hills; David Glass, White Plains, all of N.Y.

[73] Assignee: Regeneron Pharmaceuticals, Inc., Tarrytown, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/820,684

[22] Filed: Mar. 18, 1997

Related U.S. Application Data

[63] Continuation of application No. 08/544,559, Oct. 18, 1995, abandoned, which is a continuation of application No. 08/327,923, Oct. 24, 1994, abandoned.

[51] Int. Cl.[7] .................. A61K 38/16; C07K 14/435; C07K 14/475

[52] U.S. Cl. .................. 514/2; 514/12; 514/21; 530/399; 530/350

[58] Field of Search .................. 514/12, 21, 2; 530/399, 350

[56] References Cited

U.S. PATENT DOCUMENTS

| | | | |
|---|---|---|---|
| 5,004,805 | 4/1991 | Ghoda et al. | 530/399 |
| 5,532,156 | 7/1996 | Talbot et al. | 435/325 |
| 5,635,177 | 6/1997 | Bennett et al. | 424/123.1 |
| 5,650,415 | 7/1997 | Tang et al. | 514/312 |

FOREIGN PATENT DOCUMENTS

| 9104316 | 4/1991 | WIPO . |
|---|---|---|

OTHER PUBLICATIONS

Database cancerlit on STN, AN No. 91673131 Cnacerlit: Zarnegar et al. Proc. Annu. Meet. Am. Caner Res. vol. 32, PPA 1305 (1991).

Yuen et al. 'Therapeutic Potential of Neurotrophic Factors for Neurological Disorders', Annals Neurology, vol. 40 No. 3, pp 346–354, Sep. 1996.

Hefti, Franz. 'Nerothrophic Factor Therapy for Nervous System Degerative Diseases', Journal of Neurobiology, vol. 25, No. 11, pp. 1418–1435, 1994.

Horie et al. 'Hepatocytes Enhance Neurite Regeneration and Survival From Trnsected Nerve Terminals', NeuroReport, vol. 2, pp. 521–524, Sep. 1991.

Zarnegar et al. Proc. Annu. Meet. Am. Cancer Res. vol. 32, PPA1305 (1991). Abstract.

*Primary Examiner*—Christopher S. F. Low
*Assistant Examiner*—Anish Gupta
*Attorney, Agent, or Firm*—Gail M. Kempler; Robert J. Cobert

[57] ABSTRACT

The present invention provides for a method of promoting motor neuron survival, growth or differentiation comprising treating motor neurons with an effective amount of HGF. The invention also provides for a method of promoting motor neuron survival, growth or differentiation comprising treating motor neurons with an effective amount of HGF and an effective amount of CNTF. The invention further provides for a method of alleviating the toxic effects of vincristine on motor neurons comprising treating motor neurons with an effective amount of HGF and an effective amount of CNTF. The methods may be carried out in vitro or in vivo. The invention also provides a method of treating a motor neuron disorder in a patient comprising administering to the patient an effective amount of HGF and CNTF. The invention further provides a pharmaceutical composition for treating a motor neuron disorder in a patient comprising HGF and CNTF in a pharmacologically acceptable carrier.

4 Claims, 10 Drawing Sheets

METHODS OF USING HEPATOCYTE GROWTH FACTOR TO PROMOTE SURVIVAL, GROWTH AND DIFFERENTIATION OF MOTOR NEURONS

This is a continuation of application Ser. No. 08/544,559 filed Oct. 18, 1995, now abandoned, which is a continuation of application Ser. No. 08/327,923 filed Oct. 24, 1994, now abandoned.

Throughout this application various publications are referenced. The disclosures of those publications in their entireties are hereby incorporated by reference into this application.

INTRODUCTION

The present invention relates to methods of promoting motor neuron survival, growth or differentiation comprising treating motor neurons with an effective amount of hepatocyte growth factor (HGF). This invention also relates to methods of promoting motor neuron survival, growth or differentiation comprising treating motor neurons with an effective amount of hepatocyte growth factor (HGF) in combination with ciliary neurotrophic factor (CNTF). It also provides for a method of alleviating the toxic effects of vincristine on motor neurons comprising treating vincristine intoxicated motor neurons with an effective amount of HGF in combination with CNTF. It further provides for a method of treatment of a motor neuron disorder comprising administering to a patient in need of such treatment an effective amount of HGF in combination with CNTF. It also provides for a pharmaceutical composition comprising HGF and CNTF in a pharmacologically acceptable carrier.

BACKGROUND OF THE INVENTION

The interaction between motor neurons and muscle cells determines muscle tone and effects muscular contraction, and thereby underlies all voluntary and involuntary movement.

Motor neurons are traditionally classified as upper motor neurons or lower motor neurons. Upper motor neurons reside in the precentral gyrus of the brain, and send long processes down to synapse on lower motor neurons in the ventral (anterior) horns of the grey matter of the spinal cord. From the ventral horns of the spinal cord, axon processes of lower motor neurons coalesce to form the ventral roots. These axons eventually terminate on one or more muscle fibers. Through arborization of the terminal part of its fiber, each lower motor neuron comes in contact with anywhere from a few to 100–200 or more muscle fibers to form a "motor unit," (Adams and Victor, 1985, in "Principles of Neurology," McGraw-Hill, Inc., New York, p. 37).

Motor neuron disorders result in varying degrees of muscle weakness, causing disability which ranges from slight difficulty performing difficult tasks to total paralysis. Lower motor neuron disorders are generally associated with a flaccid paralysis and decrease in muscle tone. Contiguous groups of muscles, innervated by single nerves or whose motor neurons lie close together in the spinal cord, may be affected and atrophy may be quite profound, up to 70–80 percent of total bulk. A diseased motor neuron may become irritable and muscle fibers that it controls may discharge sporadically, in isolation from other units, to produce a visible twitch or fasciculation. In contrast, when upper motor neurons are damaged, a spastic paralysis with increase in muscle tone and hyperactive tendon reflexes generally results. Usually, an entire limb or half of the body, rather than individual muscle groups, is affected. Atrophy is slight and typically results from lack of use. Fasciculations are absent. The identification of a clinical syndrome as representing upper or lower motor neuron damage may facilitate its diagnosis and management.

A wide array of neurological disorders may affect motor neurons. Upper motor neurons, for example, are predominantly affected by cerebrovascular accidents, neoplasms, infections and trauma. Lower motor neurons, or anterior horn cells, are secondarily affected by these processes, but in addition are subject to a number of disorders in which anterior horn cell loss is the primary feature, including amyotrophic lateral sclerosis, infantile and juvenile spinal muscular atrophy, poliomyelitis and the post-polio syndrome, hereditary motor and sensory neuropathies, and toxic motor neuropathies (e.g. vincristine intoxication).

The vinca alkaloid vincristine sulfate is a widely used cancer chemotherapeutic agent that commonly produces a mixed sensorimotor polyneuropathy. Electrophysiological studies performed on patients treated with vincristine showed that the drug caused slowing of motor conduction and impairment of sensory conduction in peripheral nerves (McLeod and Penny, 1969). Vincristine is often the drug of choice for its anti-neoplastic properties because, unlike many anticancer drugs, it is neither emetic nor myelotoxic. However, its use is limited by neurotoxicity for which no specific antidotes have been established. Currently, the only known treatment for neurotoxicity associated with vincristine use has been the discontinuation or reduction of the dose or frequency of administration, or both, of this agent. There have been attempts to decrease vincristine toxicity by treatment with thiamine (Kaplan and Wiernik, 1982), B12 (Kaplan and Wiernik, 1982), folinic acid (Jackson et al., 1983), pyridoxine (Jackson et al., 1984), glutamic acid (Jackson et al., 1988), and ganglioside (Favaro et al., 1988), but motor neuropathy has not been addressed specifically.

Ciliary neurotrophic factor (CNTF) has been observed to promote the survival of embryonic motor neurons (Arakawa et al., 1990, J. Neurosci. 10:3507–3515; Oppenheim et al., 1991, Science 251:1616–1618; Wong et al., 1991, Neurology 41(Supplement 1):696P), prevent the degeneration of facial nerve motor neurons after axotomy (Sendtner et al., 1990, Nature 345:440–441), and allay the progression of motor neuron disease in wobbler (Mitsumoto et al., 1994, Science 265: 1107–1110) and PMN (Sendtner et al., 1992, Nature 358:502) strains of mice. CNTF is one of a number of proteins which exert trophic effects on certain components of the nervous system. The name, CNTF, derives from the first noted activity of this protein: its ability to support the survival of dissociated chick ciliary ganglion cells in culture (Manthorpe and Varon, 1985, in "Growth and Maturation Factors," vol. 3, Guroff ed., John Wiley and Sons, New York, pp. 77–117). Human CNTF, a 200 amino acid residue protein, has been cloned and characterized (Masiakowski et al., International Publication No. WO 91/04316, Int. Appln. No. PCT/US90/05241, published Apr. 4, 1991; Collins et al., U.S. Pat. No. 5,011,914, issued Apr. 30, 1991; Masiakowski et al., 1991, J. Neurochem. 57:1003–1011).

As shown in PCT Publication No. WO 91/04316, published Apr. 4, 1991 and incorporated by reference herein, ciliary neurotrophic factor (CNTF) is capable of promoting the survival of motor neurons in vitro and in vivo. Gelfoam implants containing CNTF facilitated the survival of motor neurons in severed facial nerves of newborn rats. Although it is a neurotrophic factor, CNTF exhibits biological activities that are very different from those exhibited by the neurotrophin family of factors, including brain derived neurotrophic factor (BDNF), neurotrophin-3 (NT-3), and nerve growth factor (NGF).

By comparison, hepatocyte growth factor (HGF), also referred to as hepatopoietin A, was originally identified in the serum of partially hepatectomized rats as a potent mitogen for cultured rat hepatocytes (Nakamura et al., 1984; Michalopoulos et al., 1984). HGF has subsequently been purified from rat platelets (Nakamura et al., 1986), human plasma (Gohda et al., 1988; Zarnegar and Michalopoulos, 1989), and rat liver (Asami et al., 1991), and its amino acid sequence has been deduced by cDNA cloning (Nakamura et al., 1989; Miyazawa et al., 1989; Tashiro et al., 1990; Seki et al., 1990). Several reports have revealed closed sequence homology between HGF and scatter factor (SF) (Gherardi and Stoker, 1990; Weidner et al., 1990; Rosen et al., 1990; Coffer et al., 1991), a polypeptide that stimulates dissociation of epithelial cell colonies in monolayer culture (Stoker et al., 1987; Gherardi et al., 1989). Evidence indicating that the 2 factors have identical structure and biological activities has also been presented (Weidner et al., 1991; Naldini et al., 1991; Furlong et al., 1991). Until recently, HGF was considered to have a narrow target cell specificity and to act primarily as a humoral mediator of liver regeneration after partial hepatectomy or hepatic injury.

However, it is possible that HGF is a multifunctional polypeptide that may act in a wide variety of cells, including microglia (DiRenzo et al., 1993) and skeletal muscles (Jennische et al., 1993). Furthermore, it has been shown (Stern and Ireland, 1993) that HGF can cause cultured chick ectodermal cells to become neural, raising the possibility that HGF could be a neural inducing signal during the early development of vertebrate embryos. These observations indicate a possible role for HGF in the developing and/or injured nervous system.

HGF receptor has been recently identified as the c-met protooncogene product (Bottaro et al., 1991; Naldini et al., 1991), a transmembrane protein of 190 kD ($p190^{MET}$), composed of 2 disulfide-linked chains: an extracellular 50 kD alpha subunit ($p50\alpha$) and a transmembrane 145 kD beta subunit ($p145\beta$) endowed with tyrosine kinase activity (Gonzatti-Haces et al., 1988). It is expressed in a wide variety of tissues, most predominantly in tissues of epithelial origin (Chan et al., 1988; Iyer et al., 1990). Recent reports have shown that met is also localized in many cells of neuronal origin, including spinal cord (Sonnenberg et al., 1993), hippocampus, cerebellum, forebrain, cortex, and choroid plexus (Schirmacher et al., 1993) of the developing rat brain, indicating possible roles for HGF on a wide spectrum of cells in the central nervous system.

SUMMARY OF THE INVENTION

The present invention provides for a method of promoting motor neuron survival, growth or differentiation comprising treating motor neurons with an effective amount of HGF. The invention also provides for a method of promoting motor neuron survival, growth or differentiation comprising treating motor neurons with an effective amount of HGF and an effective amount of CNTF. The invention further provides for a method of alleviating the toxic effects of vincristine on motor neurons comprising treating motor neurons with an effective amount of HGF and an effective amount of CNTF. The methods may be carried out in vitro or in vivo. The invention also provides a method of treating a motor neuron disorder in a patient comprising administering to the patient an effective amount of HGF and CNTF. The invention further provides a pharmaceutical composition for treating a motor neuron disorder in a patient comprising HGF and CNTF in a pharmacologically acceptable carrier.

ABBREVIATIONS

The following abbreviations are used herein:

BDNF brain derived neurotrophic factor
CAT choline acetyltransferase
HGF hepatocyte growth factor
NGF nerve growth factor
CNTF ciliary neurotrophic factor

BRIEF DESCRIPTION OF THE FIGURES

FIG. 9 shows number of labelled sciatic motoneurons seen in frozen sections of lumbosacral spinal cord after 9 day survival.

DETAILED DESCRIPTION OF THE INVENTION

Figure 1:
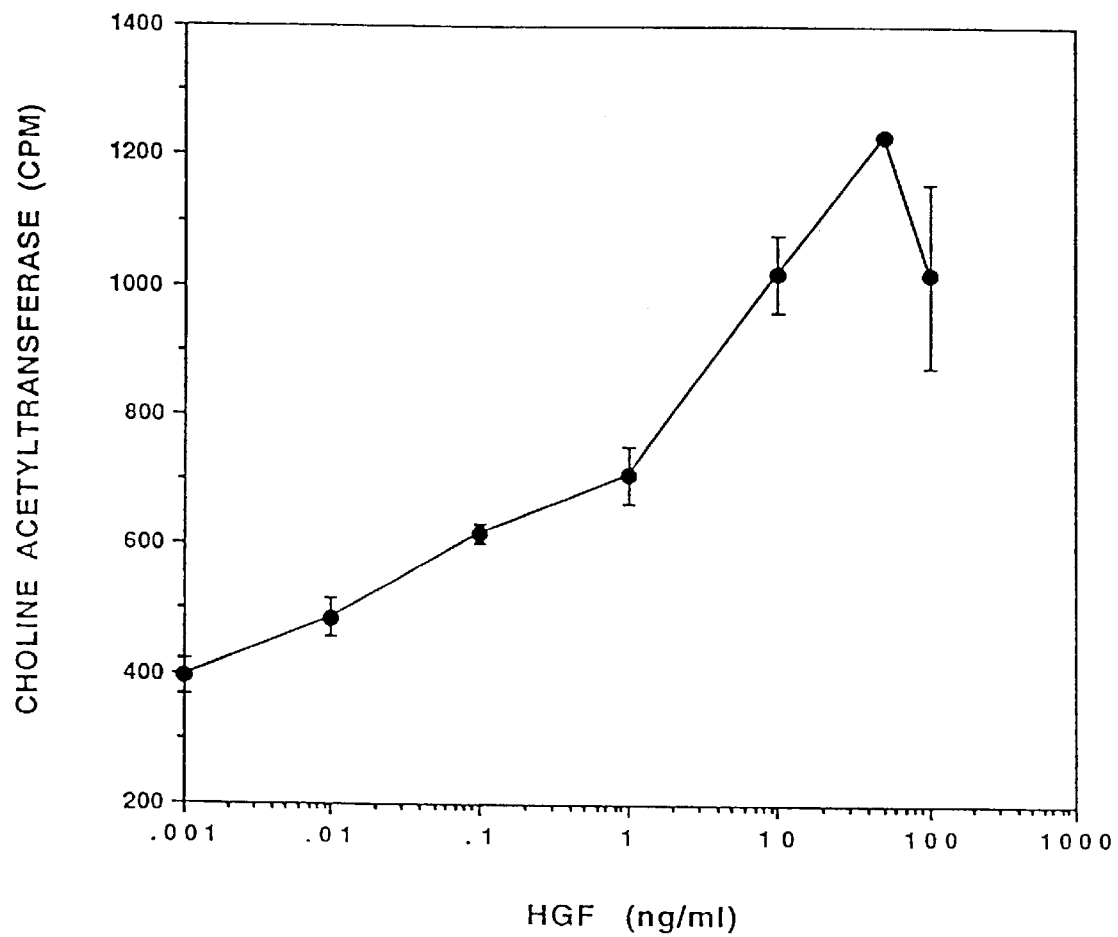
FIG. 1. Motor neuron enriched cultures were treated with various concentrations (from 10 pg/ml to 100 ng/ml) of HGF on day 0 and assayed on day 2 for CAT activity (cpm±SEM). n=3.

The present invention involves the identification of two hitherto unsuspected properties of HGF, the ability to promote survival and differentiation of motor neurons during development as well as after vincristine intoxication. The invention further involves the discovery that HGF and CNTF act synergistically to alleviate neurotoxic effects on motor neurons in vitro. When administered in combination, HGF and CNTF may improve the therapeutic efficacy of vincristine by allowing an increase of vincristine dose intensity as well as by providing greater patient comfort.

The present invention provides a method of promoting motor neuron survival, growth or differentiation comprising treating motor neurons with an effective amount of HGF. The method may be carried out in vitro or in vivo.

The invention further provides a method of promoting motor neuron survival, growth or differentiation comprising treating motor neurons with an effective amount of HGF and an effective amount of CNTF. The method may be carried out in vitro or in vivo.

The invention also provides for a method of alleviating the toxic effects of vincristine on motor neurons comprising treating motor neurons with an effective amount of HGF and an effective amount of CNTF. The method may be carried out in vitro or in vivo.

In in vitro embodiments, effective amounts of a composition comprising HGF or a composition comprising HGF+CNTF may desirably be determined on a case by case basis, as motor neurons from different tissue sources or from different species may exhibit different sensitivities. For any particular culture, it may be desirable to construct a dose response curve that correlates the concentration of the composition with motor neuron response. To evaluate motor neuron survival, growth, and/or differentiation, it may be useful to compare motor neurons exposed to the composition to motor neurons not exposed to such composition, using, for example, vital dyes to evaluate survival, phase-contrast microscopy and/or neurofilament stain to measure neurite sprouting, or techniques that measure the bioactivity of motor neuron-associated compounds, such as choline acetyltransferase (CAT).

The invention further provides a method of treating a motor neuron disorder in a patient comprising administering to the patient an effective amount of HGF and CNTF. The HGF and CNTF may be coadministered or they may be administered separately, either on the same day or on alternate days. The motor neuron disorder may be caused by amyotrophic lateral sclerosis, trauma, progressive spinal muscular atrophy, infantile or juvenile muscular atrophy, poliomyelitis, post polio syndrome, Charcot-Marie-Tooth disease or vincristine intoxication.

The invention also provides for a pharmaceutical composition for treating a motor neuron disorder in a patient comprising HGF and CNTF in a pharmacologically acceptable carrier. Pharmaceutical compositions for use according to the invention include HGF or HGF+CNTF comprised in a liquid, solid, or semi-solid solution. For example, the pharmaceutical composition may comprise HGF+CNTF in an aqueous solution, such as sterile water, saline, phosphate buffer or dextrose solution. Alternatively, HGF+CNTF may be comprised in a solid (e.g. wax) or semi-solid (e.g. gelatinous) formulation that may be implanted into a patient in need of such treatment. Preferably, an aqueous solution of the pharmaceutical composition would be administered by subcutaneous injection.

Administration may result in the distribution of the composition of the invention throughout the body or in a localized area. For example, in some conditions which involve distant regions of the nervous system, intravenous or intrathecal administration of the composition may be desirable. Alternatively, when localized regions of the nervous system are involved, such as in motor neuron disorders caused by trauma or surgery, local administration may be desirable. In such situations, an implant containing the composition may be placed in or near the lesioned area. Suitable implants include, but are not limited to, gelfoam, wax, or microparticle-based implants.

An aqueous solution of the composition may be administered by subcutaneous injection. Each dose may range from about 0.5 to about 1000 $\mu$g per kilogram body weight, including all ranges subsumed therein. When HGF is used in combination with human CNTF, the CNTF dose range will likely be from about 0.5 $\mu$g to about 50 $\mu$g rHCNTF per kilogram of body weight (assuming rHCNTF has an $EC_{50}$= 200 pg/ml, as assayed by Manthorpe et al., 1986, Dev. Brain Res. 25:191), including all ranges subsumed therein. The dosing schedule for subcutaneous administration of factors may vary from one a week to several daily injections based upon the severity of the disease and the patient's sensitivity to the treatment.

Certain standard techniques are available in the art to determine the optimal administration of a medication as set forth by Fingl, et al., *The Pharmacological Basis of Therapeutics*, ed. by Goodman and Gilman, pp. 1–46 (1975). Fingl, et al. teach the pharmacokinetic factors that should be considered when determining the use of a therapeutic agent, such as absorption, distribution, biotransformation, determination of dosage and excretion of drugs. Various routes of administration are explained in detail. Fingl, et al., also teach consideration of the metabolism, the determination of the volume of distribution, the effective and lethal doses of a drug, and other pharmacodynamic factors such as the dose-effect relationship and potency, as well as clinical considerations in the development and evaluation of new therapeutic agents.

The choice of treatment regimen for a particular patient may be made based on the severity of the patient's disease, his individual responses to treatment (e.g. side effects or rate of change of clinical condition), and his availability in the clinic or hospital. Under certain circumstances, for example, involving severe disease, it may be desirable to administer the treatment intravenously or intrathecally. Continuous infusion may be appropriate. Alternatively, the patient may exhibit side effects. For example, although rHCNTF in the dose range of 0.5 $\mu$g/kg to about 50 $\mu$g/kg has been generally well tolerated by human patients, some patients have exhibited low-grade temperature elevations, cold-like symptoms, cold sores and fatigue, and two patients exhibited an irregular heartbeat. It may desirable to administer a lower dose at more frequent intervals to patients that exhibit such effects. Alternatively, the composition may be administered concurrently with an antipyretic agent such as aspirin, acetaminophen, or a nonsteroidal anti-inflammatory drug, so as to reduce fever and thereby permit a given dose to be better tolerated or to allow administration of greater doses. Further, the pharmaceutical composition may be administered concurrently with an antipyretic agent such as aspirin, acetaminophen, or a nonsteroidal anti-inflammatory drug, so as to permit a given dose to be better tolerated or to allow administration of larger doses. The clinical effects of treatment in a patient may be determined using any quantitation of muscle force generation by assessment of a patient's functional abilities or pulmonary function tests. Such methods may be used to evaluate a patient's response and thereby optimize the dosing schedule during therapy.

It is anticipated that the steps to be taken in determining a treatment regimen will be similar to those taken in treating patients with CNTF. For example, in treating amyotrophic lateral sclerosis (ALS), muscle strength may be tested in each patient prior to receiving their first dose of study medication, and then again 4 weeks later. Evaluation in the clinic may consist of measurement of maximum voluntary isometric contraction (Munsat et al., 1988, Neurol. 38:409; Brooks et al., 1991, Adv. Neurol. 56:521). Briefly, patients may be positioned on an examination table, and a strap affixed to various positions on the limbs appropriate to test the muscle groups to be studied. The strap may pull on a strain gauge (SM-250 Mini Load Cell, Interface Corp., Scottsdale, Ariz.), the output of which can be led to a Macintosh computer programmed to record the maximum force generated by the patient in each of 4 movements bilaterally, to yield a total of 8 measurements: shoulder flexion, elbow flexion, hip flexion and knee extension. In addition to muscle strength, Forced Vital Capacity ("FVC") may be used as a measure of pulmonary function. FVC may be measured using a portable spirometer (Puritan-Bennet model PB100).

MATERIALS AND METHODS
MOTOR NEURON ENRICHED CULTURE:

Cultures enriched for motor neurons were prepared from E14 rat embryos as described by Wong et al., European Journal of Neuroscience 5: 466–474 (1993).

CHOLINE ACETYLTRANSFERASE ASSAY:

Cultures were harvested and assayed as described by Wong et al., European Journal of Neuroscience 5: 466–474 (1993).

Treatments were initiated on day 0 and cultures were harvested on day 2, unless otherwise stated.

IMMUNOCYTOCHEMICAL STAINING FOR $p75^{LNGFR}$:

Cultures were washed twice with PBS and fixed with 4% paraformaldehyde for 20 min. Non-specific protein binding was blocked by incubating cultures in 10% normal goat serum in PBS (pH 7.4) for 1 hr. The cultures were then incubated with a rabbit polyclonal antibody against the intracellular domain of the LNGFR molecule at a dilution of 1:15,000 for 48 hrs. at 4° C. The bound rabbit immunoglobulin (Ig) was detected using a biotinylated goat-anti-rabbit IgG (1:200) (Vector Laboratories, Inc., Burlingame, Calif.), followed by peroxidase-conjugated avidin (1:500; Vector ABC Kit). Immunoreactivity was visualized using diaminobenzidine as the substrate for the bound peroxidase enzyme, followed by intensification with nickel sulfate. Cell counts were performed under 32× objective lens, with the aid of a 0.45 mm grid.

HIGH AFFINITY CHOLINE UPTAKE:

Choline uptake via a high-affinity, Na+-dependent mechanism was assayed by the procedure described by Alderson et al., Neuron 5: 297–306 (1990).

RNA ISOLATION AND NORTHERN BLOTTING ANALYSIS:

Total RNA from motor neuron cultures was isolated by GTC extraction method as described by Chomczynski, P. and Sacchi, N., Anal. Biochem. 162: 156–159 (1987). Total RNA from rat spinal cord tissues was isolated as described by Maisonpierre et al., Neuron 5: 501–509 (1990). Five to ten micrograms of total RNA was electrophoresed in 1% agarose/2.2M formaldehyde gels, transferred to nylon membranes in 6× SSC and UV cross-linked (0.1 joule). Blots were prehybridized, hybridized and washed as previously described (Maisonpierre et al., 1990). The c-met probe used in this study was DNA fragments which spanned the region encoding the tyrosine kinase domain. The plasmid insert was isolated after restriction endonuclease digestion, separated by agarose gel electrophoresis, and purified by electroelution. $^{32}P$-labelled cDNA probe with specific activity of 2–5×10$^9$ cpm/μg were prepared by primer extension with random hexamers using the Prim-a-gene kit (Promega) according to the manufacturer's instructions.

TROPHIC FACTORS:

Recombinant human BDNF was obtained from Amgen, Inc. (Thousand Oaks, Calif.). Recombinant rat CNTF was expressed and purified as described by Masiakowski et al., J. Neurochem. 57: 1003–1012 (1991). HGF was obtained from R & D Systems, Inc. (Minneapolis, Minn.). The biological activities of CNTF and BDNF were verified routinely by bioassay on dissociated cultures of E8 chick embryonic ciliary ganglion and dorsal root ganglion neurons respectively.

IN VIVO STUDY—SURGERY, HISTOLOGY AND MOTONEURON COUNTING

Surgery, histology and motoneuron counting were performed by Dr. Ann Kato of the Department of Pharmacology of the University of Geneva according to the procedure described by Vejsada, R., et al., Eur. J. Neurosi. Vol. 6 (1994). In general, the left sciatic nerve was sectioned in the mid-thigh in anaesthetized 6 day old (postnatal day 6) rats of the Sprague-Dawley strain. A small polyethylene tube was filled with 3 μl of a freshly prepared mixture of fluoro-gold (Fluorochrome, Englewood, Colo., USA: final concentration 2.5%) and either bovine serum albumin (BSA) or HGF (0.5 mg/ml) or BDNF (1.6 mg/ml). The incision was sutured and the rats were returned to their mother.

After 9 days of survival, the rats were killed by an overdose of pentobarbital and perfused through the heart with 4% paraformaldehyde in phosphate-buffered saline (PBS; pH 7.4): the lumbosacral spinal cord was removed and the tissue was cryoprotected by incubation in successive solutions of 12, 20, and 30% sucrose-PBS at 4° C. Cryostat serial sections (30 μm) were viewed under a Reichert-Jung fluorescent microscope using a wide-band UV filter. Fluorogold-labelled cells, identifiable as motoneurons by their size and shape, were found in the dorsolateral and mediolateral part of the left ventral horn.

RESULTS

Stimulation of Cholinergic Expression by HGF

Figure 2:
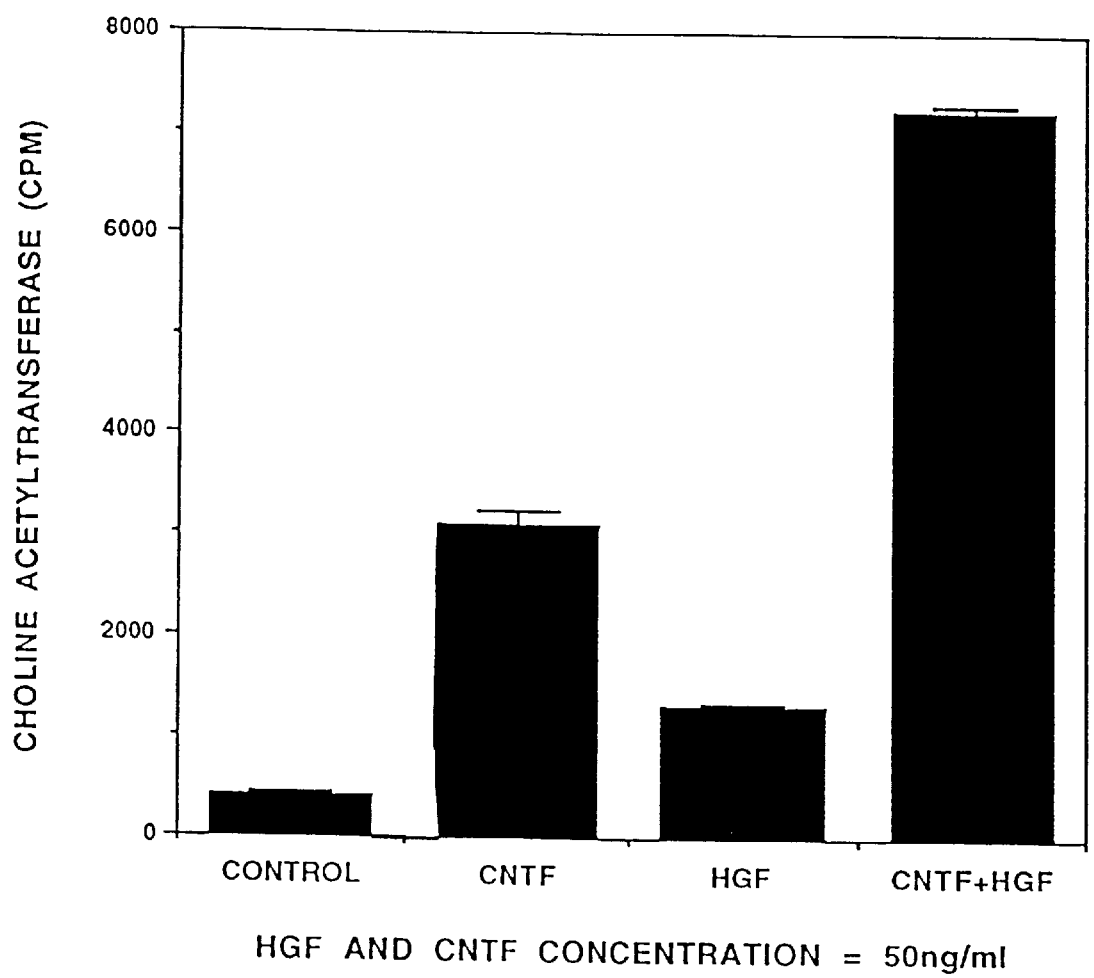
FIG. 2. Motor neuron enriched cultures were treated with CNTF, HGF, or the combination of the 2 factors (all at 50 ng/ml) on day 0. On day 2, cultures were harvested and assayed for CAT activity (cpm±SEM). n=3.

We determined that HGF stimulated cholinergic expressions in motor neurons. HGF increased CAT activity in cultured motor neurons in a dose dependent manner, attaining a maximal stimulation (2 to 3-fold) at about 50 ng/ml (FIG. 1). Co-administration of HGF and CNTF increased CAT activity synergistically, resulting in a more than 10-fold stimulation (FIG. 2).

Promotion of Motor Neuron Survival by HGF

We performed two experiments to address the possibility that increased CAT activity might be due to the rescue of cholinergic cells which ultimately degenerate in culture in the absence of appropriate growth factors, or to the induction of the cholinergic phenotype, or both.

Figure 3:
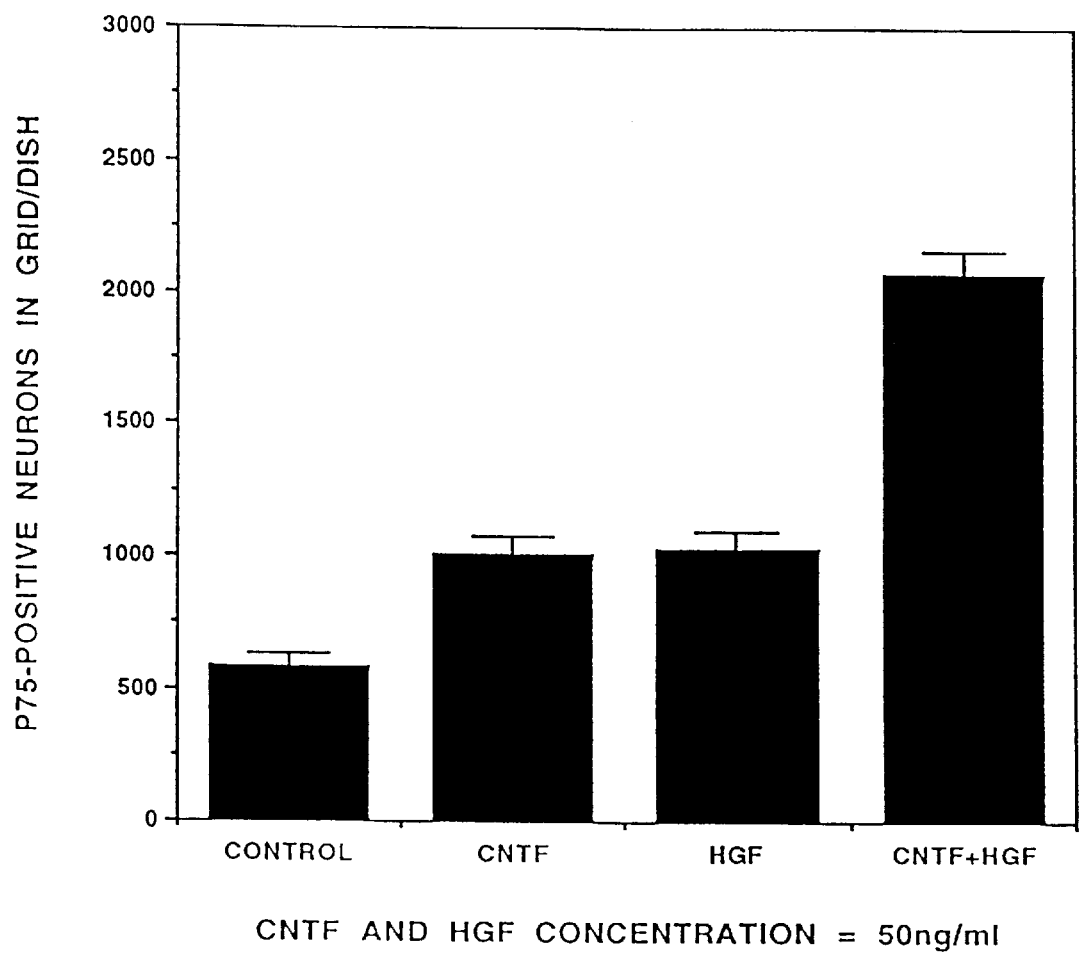
FIG. 3. Motor neuron enriched cultures were treated with CNTF, HGF, or the combination of the 2 factors (all at 50 ng/ml) on day 0. On day 5, the cultures were fixed and stained immunocytochemically for $p75^{LNGFR}$. Positively stained neurons were counted under 32× objective with the aid of a 0.45 mm grid. n=3.

Since $p75^{LNGFR}$ has been shown to be a useful motor neuron marker especially during development (Yan and Johnson, 1988), we sought to determine the number of $p75^{LNGFR}$ positive neurons in cultures maintained in the presence or absence of HGF with or without CNTF (HGF±CNTF). HGF was as effective as CNTF in supporting survival of $p75^{LNGFR}$ positive neurons, resulting in a 1.55 fold increase in cell number (FIG. 3). When HGF and CNTF were coadministered, a 4-fold increase in $p75^{LNGFR}$ positive neurons was observed (FIG. 3), suggesting that the up-regulation of CAT activity was due to increases in both motor neuron survival and differentiation.

Figure 4:
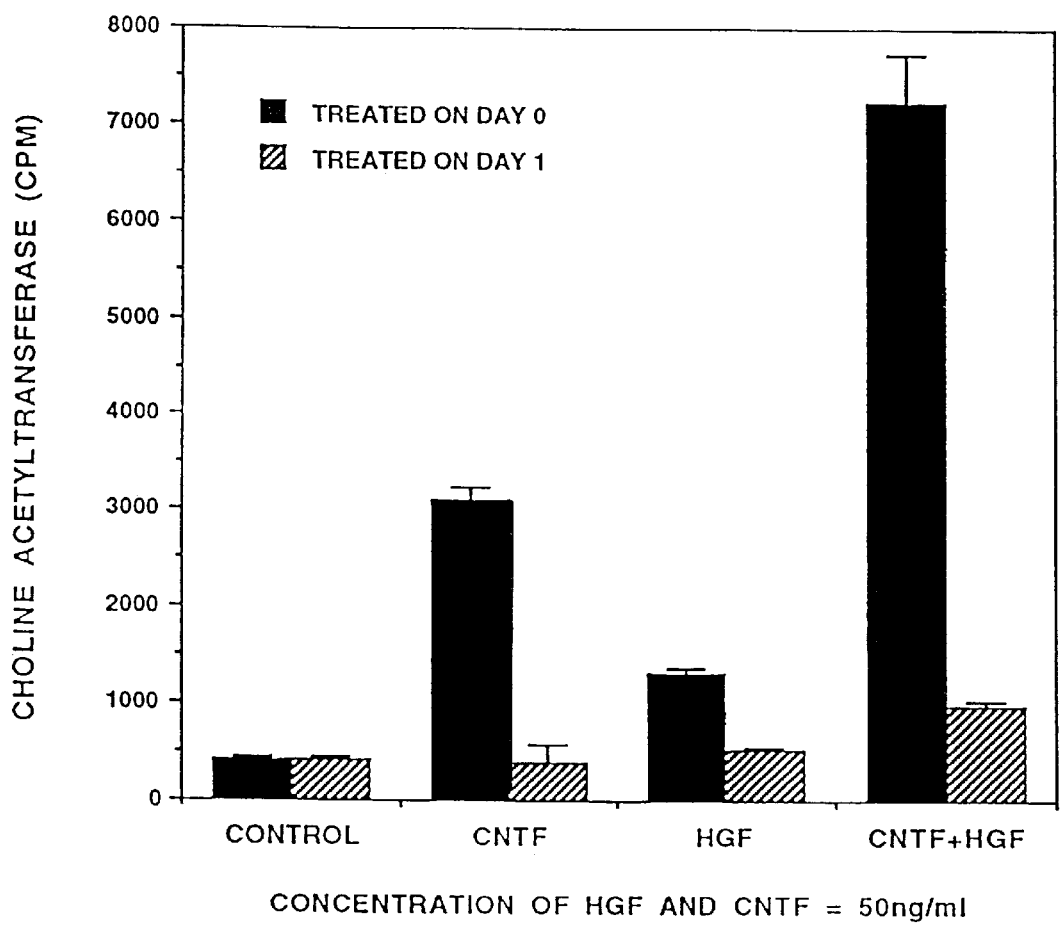
FIG. 4. Motor neuron enriched cultures were treated with CNTF, HGF, or the combination of the 2 factors (all at 50 ng/ml) either on day 0 or day 1. They were then assayed for CAT activity on day 2. n=3.

Because motor neurons in this culture system did not survive without exogenous factors, if HGF was simply up-regulating the cholinergic phenotype without supporting survival, a delayed addition of HGF±CNTF should give only an attenuated effect on CAT level because there were few motor neurons left in the dish to be affected. We found that when HGF±CNTF was added on the day of plating, a dramatic increase in CAT activity was observed (FIG. 4). However, when addition of trophic factors was delayed to day 1, the elevation of CAT activity was almost completely abolished, suggesting that the presence of HGF±CNTF is necessary to keep motor neurons alive during the first 24 hrs. (FIG. 4).

Expression of met mRNA in Spinal Cord and Cultured Motor Neurons

Figure 5A:
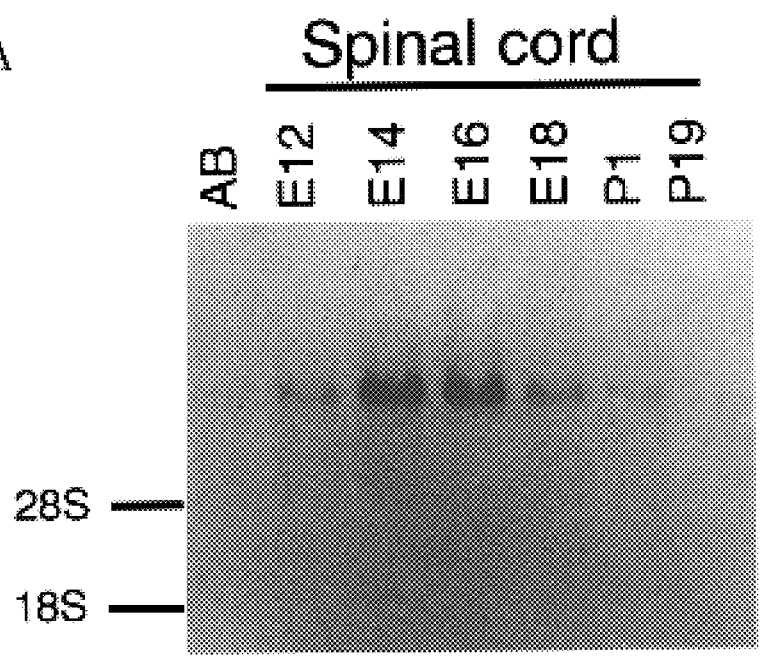
FIGS. 5A and 5B. Five micrograms of total RNA prepared from rat embryonic (E12–18) and postnatal (P1, P19) spinal cord and adult brain (AB) were loaded per lane, electrophoresed, and hybridized to met specific probe (FIG. 5A). Similarly, ventral and dorsal halves of rat E14 spinal cords and cells from motor neuron enriched cultures (MNC) were probed for met (FIG. 5B). Positions of 18S and 28S ribosomal RNA are indicated on the left.

To demonstrate that the effect of HGF on motor neurons is a physiological response mediated via specific receptor, we performed Northern blot analysis to examine the levels of c-met (HGF receptor). The expression of c-met in rat spinal cord was found to be developmentally regulated. The highest level of c-met mRNA was expressed at E14 and E16 spinal cord and gradually decreased until it virtually disappeared by P19 (FIG. 5A). The peak expression of HGF receptor appeared to coincide with the period of natural cell death of the motor neurons, suggesting a possible role in the regulation of this process.

Figure 5B:
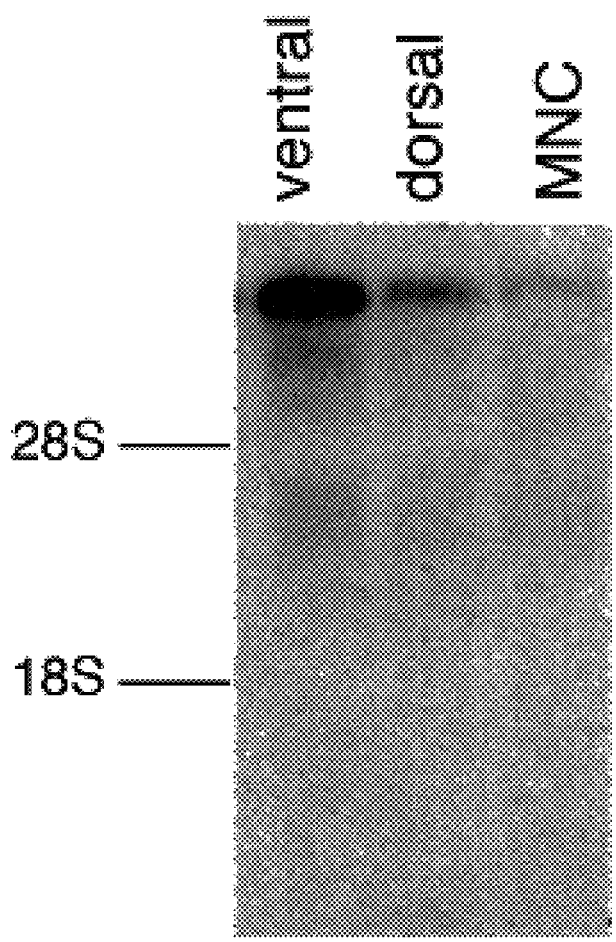

We also dissected E14 rat spinal cord into dorsal and ventral halves and detected high levels of c-met mRNA in ventral spinal cord (where the majority of spinal cord motor neurons reside) and much lower amount in the dorsal half (FIG. 5B), suggesting a predominant localization in motor neurons. This was substantiated by the fact that c-met was expressed in our motor neuron culture (FIG. 5B).

Figure 6:
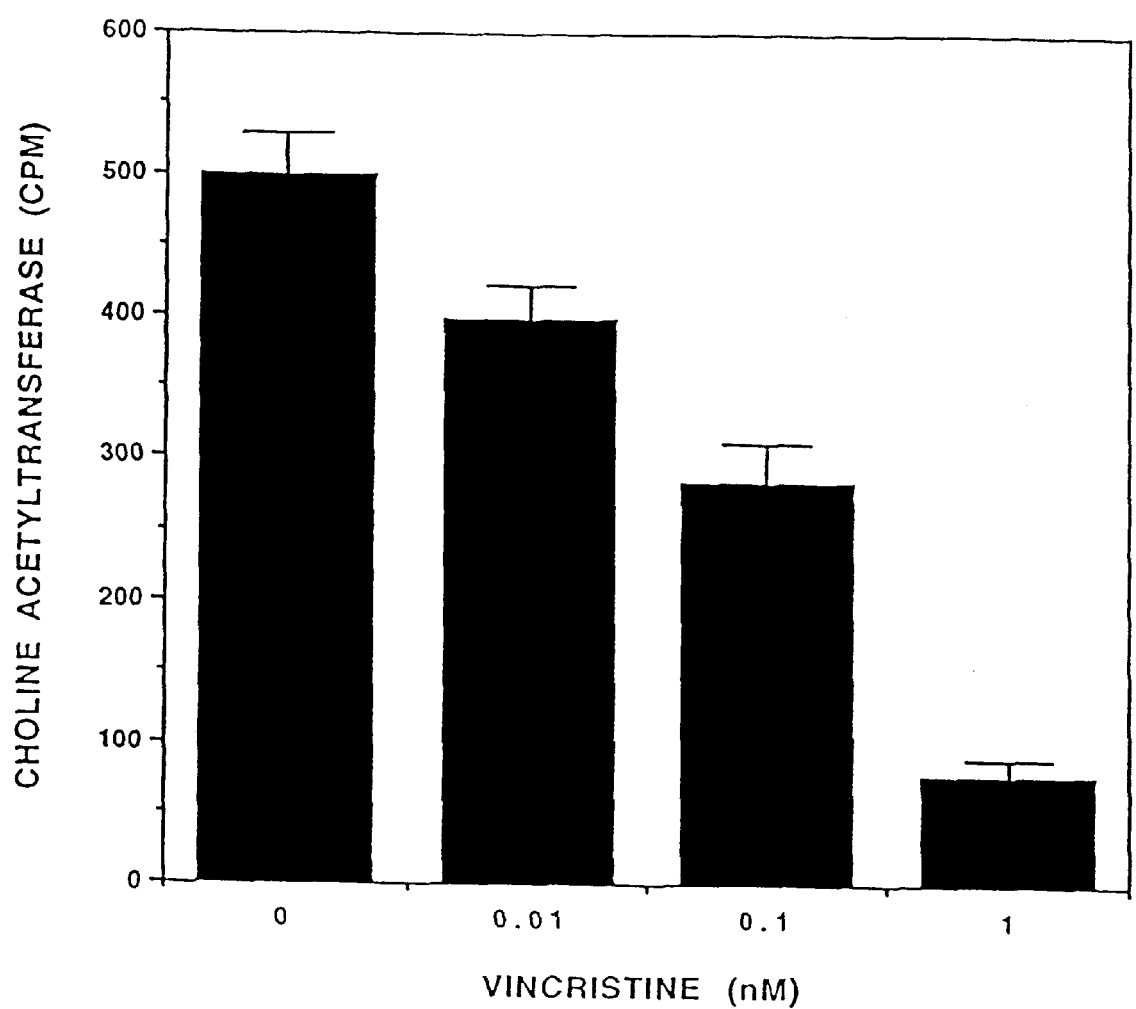
FIG. 6. Motor neuron enriched cultures were treated with various concentrations of vincristine (ranged from 10 pM to 1 nM) on day 0 and assayed for CAT activity on day 2. n=3.
Figure 7:
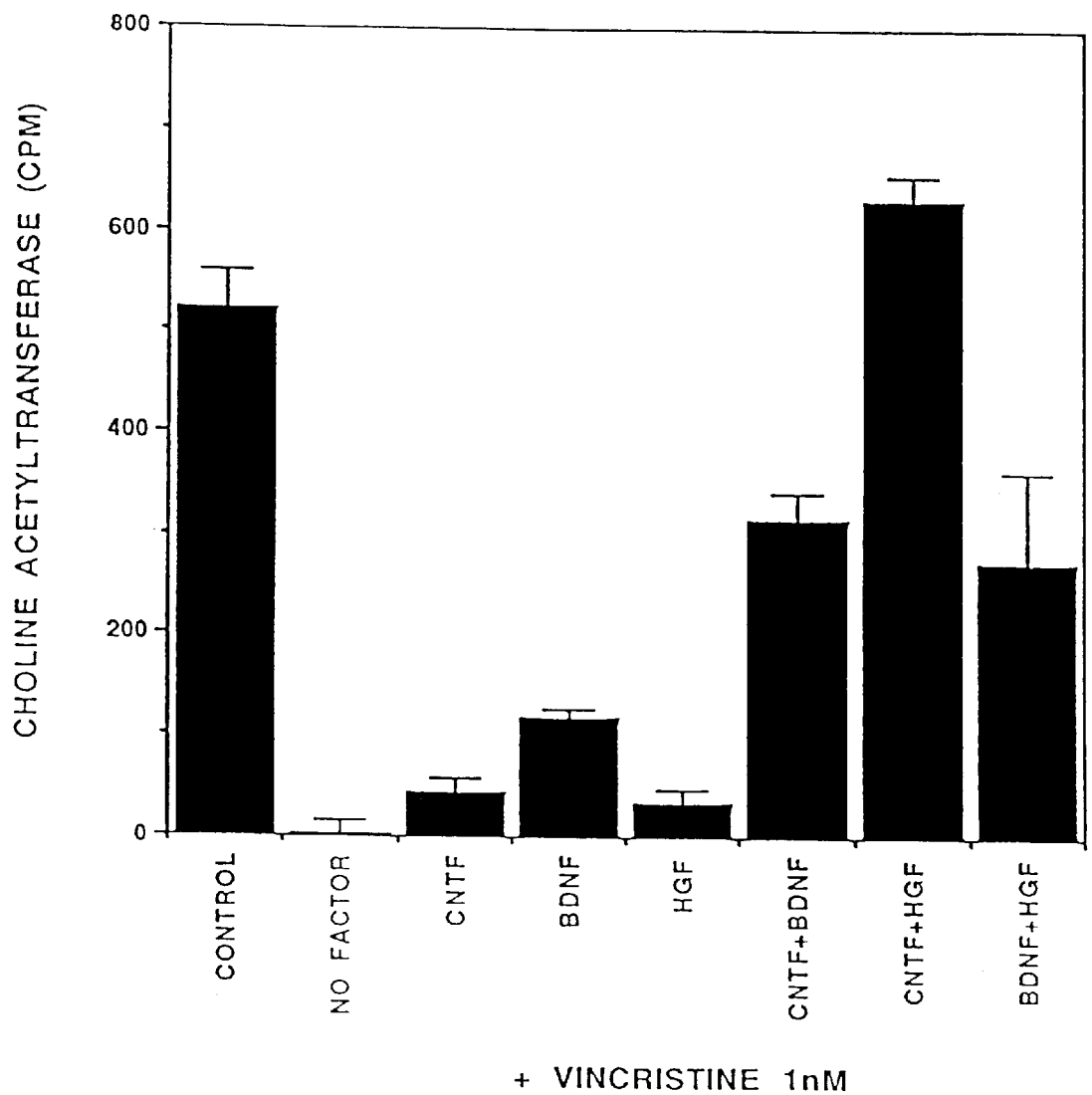
FIG. 7. Motor neuron enriched cultures were treated with vincristine (1 nM) with or without trophic factors (CNTF, BDNF, HGF, or a combination of 2 factors; all at 50 ng/ml) on day 0. Cultures without vincristine treatment (CONTROL) were also included. On day 2, cultures were harvested and assayed for CAT activity. n=3.

Dose-dependent Loss of Cholinergic Activity Due to Vincristine and Rescue by Treatment with HGF or HGF/CNTF In the presence of vincristine at 1 nM, cultured motor neurons died within 48 hours as reflected by an almost 10-fold decrease in CAT activity (FIG. 6). HGF±CNTF protected motor neurons from vincristine toxicity and preserved the cholinergic phenotype. HGF alone partially recovered CAT activity as compared to the cultures with no factor administered (FIG. 7). CNTF promoted motor neuron survival and differentiation (see FIGS. 2, 3, 4), and appeared to partially rescue motor neurons from vincristine toxicity (FIG. 7). By contrast, when HGF and CNTF were co-administered they completely rescued loss of CAT activity resulted from vincristine toxicity (FIG. 7), suggesting a synergistic effect of the two factors. This suggests that co-administration of HGF and CNTF may ameliorate motor neuropathy resulting from vincristine anti-cancer treatment.

HGF+CNTF Protects Motor Neurons from Vincristine Toxicity

Figure 8:
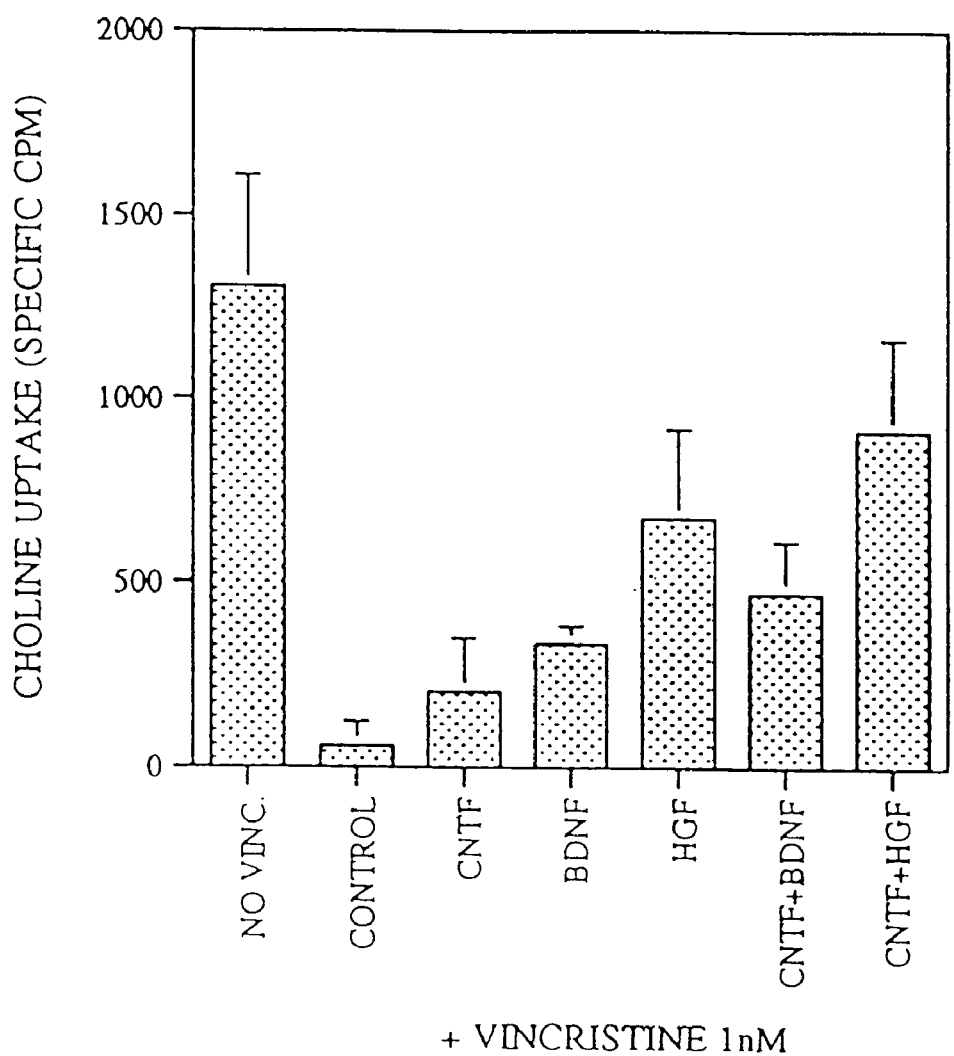
FIG. 8. Motor neuron enriched cultures were treated with vincristine (1 nM) with or without trophic factors (CNTF, BDNF, HGF, or a combination of 2 factors; all at 50 ng/ml) on day 0. Cultures without vincristine treatment (NO VINC.) were also included. On day 2, cultures were assayed for high-affinity choline uptake. n=3.

High-affinity choline uptake is a physiological process essential for the function of cholinergic neurons. When motor neurons were intoxicated by vincristine, high-affinity choline uptake was virtually abolished. However, in the presence of HGF+CNTF, high-affinity choline uptake was maintained at about 70% of no vincristine control, suggesting preservation of functions in motor neurons (FIG. 8).

Effects of HGF on the Survival of Lesioned Motoneurons In Vivo

Figure 9:
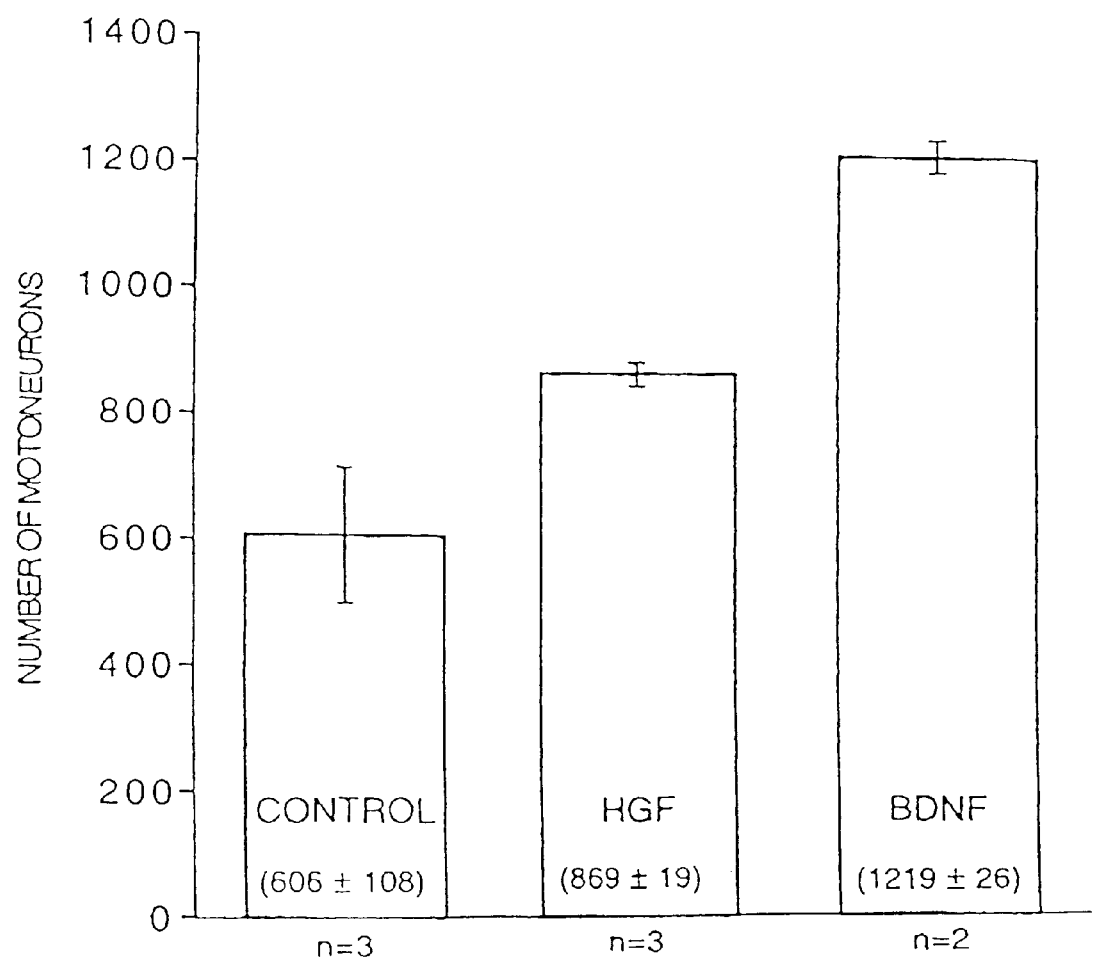
FIG. 9. Effects of HGF on the survival of lesioned motoneurons in vivo. Sciatic nerve sectioning of six day old rats followed by application of fluoro-gold label together with either BSA (controls), HGF or BDNF onto the proximal nerve stump.

As described above, the sciatic nerve of six day old rats were sectioned followed by application of fluoro-gold label together with either BSA (controls), HGF or BDNF onto the proximal nerve stump. After 9 day survival, frozen sections of lumbosacral spinal cord were examined for labelled motoneurons. FIG. 9 shows that treatment with either HGF or BDNF enhanced motoneuron survival relative to BSA controls.

It is an aspect of the present invention that HGF administered with or without CNTF (HGF±CNTF) promotes survival and differentiation of motor neurons during development. It is a further aspect that HGF and CNTF act synergistically to alleviate neurotoxic effects on cultured motor neurons caused by vincristine treatment. It is expected that co-administration of HGF and CNTF may improve the therapeutic efficacy of vincristine by allowing an increase of dose intensity as well as by providing greater patient comfort.

REFERENCES

Alderson, R. F., et al., Neuron 5: 297–306 (1990).
Asami, O., et al. , J. Biochem. 109: 8–13 (1991).
Bottaro, D. P., et al., Science 251: 802–804 (1991).
Chan, A.-L., et al., Oncogene 2: 593–599 (1988).
Chomczynski, P. and Sacchi, N. Anal. Biochem. 162: 156–159 (1987).
Coffer, A., et al., J. Biochem. 278: 35–41 (1991).
Di Renzo, M. F., et al., Oncogene 8: 219–222 (1993).
Favaro, G., et al., Toxicol. 49: 325–329 (1988).
Furlong, R. A., et al., J. Cell Biol. 100:173–177 (1991).
Gheradi, E., et al., Proc. Natl. Acad. Sci. USA 86: 5844–5848 (1989).
Gheradi, E. and Stoker, M. , Nature 346: 228 (1990).
Gohda, E., et al., J. Clin. Invest. 81: 414–419 (1988).
Gonzatti-Haces, M., et al., Proc. Natl. Acad. Sci. USA 85: 21–25 (1988).
Iyer, A., et al., Cell Growth Diff. 1: 87–95 (1990).
Jackson, D., et al., Proc. Am. Asso. Cancer Res. Abstr. 24: 276 (1983).
Jackson, D., et al., Proc. Am. Asso. Cancer Res. Abstr. 25: 313 (1984).
Jackson, D. V., et al., Am. J. Med. 84:1016–1022 (1988).
Jennische, E., et al., Am. J. Physiol. 265: C122–128 (1993).
Kaplan, R. S. and Wiernik, P. H., Semin. Oncol. 9:103–130 (1982).
Masiakowski, P. et al., J. Neurochem. 57: 1003–1012 (1991).
McLeod, J. G. and Penny, R., J. Neurol. Neurosurg. Psychiat. 32: 297–304 (1969).
Michalopoulos, G., et al., Cancer Res. 44: 4414–4419 (1984).
Miyazawa, K., et al., Biochem. Biophys. Res. Commun. 163: 967–973 (1989).
Nakamura, T., et al., Biochem. Biophys. Res. Commun. 122:1450–1459 (1984).
Nakamura, T., et al., Proc. Natl. Acad. Sci. USA 83: 6489–6493 (1986).
Nakamura, T., et al., Nature 342: 440–443 (1989).
Naldini, L., et al., EMBO J. 10: 2867–2878 (1991).
Naldini, L., et al., Oncogene 6: 501–504 (1991).
Olender, E. J. and Stach, R. W., J. Biol. Chem. 255: 9338–9343 (1980).
Rosen, E. M., et al., Proc. Soc. Exp. Biol. Med. 195: 34–43 (1990).

Schirmacher, P., et al., Soc. Neurosci. Abstr. Vol. 1, page 6 (1993).

Seki, T., et al., Biochem. Biophys. Res. Comm. 172: 321–327 (1990).

Sonnenberg, E. et al., J. Cell Biol. 123: 223–235 (1993).

Sonnenberg, E., et al., *Hepatocyte Growth Factor and the c-Met Receptor.* Ed. I. D. Goldberg and E. M. Rosen., pp. 381–394 (1993).

Stern, C. D. and Ireland, G. W., HGF-SF: A neural inducing molecule in vertebrate embryos? in *Hepatocyte Growth Factor and the c-Met Receptor,* Eds. I. D. Goldberg and E. M. Rosen, pp. 369–380 (1993).

Stoker, M., et al., Nature 327: 239–242 (1987).

Tashiro, K., et al., Proc. Natl. Acad. Sci. USA 87: 3200–3204 (1990).

Weidner, K. M., et al., J. Cell Biol. 111: 2097–2108 (1990).

Weidner, K. M., et al., Proc. Natl. Acad. Sci. USA 88: 7001–7005 (1991).

Wong, V., et al., Europ. J. Neurosci. 5: 466–474 (1993).

Yan, Q., et al., Neuron 1: 335–343 (1988).

Zarnegar, R. and Michalopoulos, G. K., Cancer Res. 49: 3314–3320 (1989).

What is claimed is:

1. A method of promoting motor neuron survival, growth or differentiation in vitro comprising administering an effective amount of HGF.

2. The method of claim 1, comprising administering an effective amount of HGF and an effective amount of CNTF.

3. A method of protecting motor neurons from the neurotoxic effects of vincristine in vitro comprising administering an effective amount of HGF and an effective amount of CNTF.

4. A composition comprising HGF, CNTF and a carrier useful for promoting motor neuron survival, growth or differentition in vitro.

* * * * *